US005849982A

United States Patent [19]
Lee et al.

[11] Patent Number: 5,849,982
[45] Date of Patent: Dec. 15, 1998

[54] RECOVERY OF STYRENE FROM PYROLYSIS GASOLINE BY EXTRACTIVE DISTILLATION

[75] Inventors: Fu-Ming Lee, Katy; Joseph C. Gentry, Houston, both of Tex.; Randi Wright Wytcherley, Belgrade, Mont.

[73] Assignee: HFM International, Inc., Houston, Tex.

[21] Appl. No.: 967,185

[22] Filed: Oct. 29, 1997

Related U.S. Application Data

[63] Continuation of Ser. No. 651,707, May 21, 1996, abandoned.

[51] Int. Cl.⁶ .............................. C07C 7/08; C07C 7/17; C07C 7/10; B01D 3/40
[52] U.S. Cl. .................. 585/833; 585/806; 585/807; 585/808; 585/857; 585/862; 585/863; 585/860; 585/864; 585/868; 585/866; 585/834; 203/53; 203/58; 203/60; 203/92; 203/90
[58] Field of Search .................. 585/806, 807, 585/808, 833, 857, 862, 863, 860, 868, 864, 866, 834; 203/53, 58, 60, 92, 90

[56] References Cited

U.S. PATENT DOCUMENTS

| | | | |
|---|---|---|---|
| 2,380,019 | 7/1945 | Bloomer | 202/42 |
| 2,385,235 | 9/1945 | Schneider | 202/42 |
| 2,467,197 | 4/1949 | Engel | 202/42 |
| 2,480,919 | 9/1949 | Greene | 202/42 |
| 2,753,381 | 7/1956 | Nelson | 260/666 |
| 2,831,039 | 4/1958 | Nevitt | 260/674 |
| 2,943,122 | 6/1960 | Templeman et al. | 260/647 |
| 3,018,228 | 1/1962 | Cornell | 202/39.5 |
| 3,210,259 | 10/1965 | Cornell et al. | 202/39.5 |
| 3,272,723 | 9/1966 | Fannin | 203/51 |
| 3,328,267 | 6/1967 | Muller | 203/43 |
| 3,684,665 | 8/1972 | Abe et al. | 203/9 |
| 3,763,015 | 10/1973 | Morimoto et al. | 203/9 |
| 3,953,300 | 4/1976 | Ginnasi et al. | 203/53 |
| 4,031,153 | 6/1977 | Haskell | 260/669 A |
| 4,371,427 | 2/1983 | Holler et al. | 203/3 |
| 4,401,517 | 8/1983 | Lee | 203/53 |
| 4,514,261 | 4/1985 | Crum | 204/9 |
| 4,543,437 | 9/1985 | Henery et al. | 585/857 |
| 4,543,438 | 9/1985 | Henery et al. | 585/857 |
| 4,959,128 | 9/1990 | Berg | 203/57 |
| 4,966,656 | 10/1990 | Berg | 203/60 |
| 5,100,514 | 3/1992 | Berg et al. | 203/14 |
| 5,399,244 | 3/1995 | Gentry et al. | 203/73 |

FOREIGN PATENT DOCUMENTS 49-16408  4/1974  Japan.

OTHER PUBLICATIONS

SRI Report #33A, Section 8, pp. 109–128, "Recovery of Styrene from Pyrolysis Gasoline". Mar. 1973.
Handbook of Chemistry and Physics; David R. Lide; 75th edition, 1995.
SRI Report #33 A, Section 8, pp. 109–128, "Recovery of Styrene from Pyrolysis Gasoline" (Mar. 1973).
Hydrocarbon Processing, Masaki Sato, Toray Industries, Inc., Tokyo, pp. 141–144, "Extract Styrene from Pyrolysis Gasoline" (May 1973).
Request for Quotation, Badger, specifically Process Duty Specification for Column Item No. C–281 (Oct. 1994).
Toray Industries, Inc., Petrochemical Laboratory, Yoshio Yamanaka et al., (5 pages), "The STEX Process—A New Styrene Production Process Developed by Toray" (date not known).

*Primary Examiner*—Glenn Caldarola
*Assistant Examiner*—Thuan D. Dang
*Attorney, Agent, or Firm*—Jenkens & Gilchrist, P.C.

[57] ABSTRACT

An extractive distillation process for separating at least one substituted unsaturated aromatic from a pyrolysis gasoline mixture, containing said aromatic and at least one close-boiling aromatic or non-aromatic hydrocarbon, employing a two part extractive solvent, the first part selected from propylene carbonate, sulfolane (tetramethylene sulfone), methyl carbitol, 1-methyl-2-pyrrolidinone, 2-pyrrolidinone and mixtures thereof, and the second portion consisting of water.

16 Claims, 4 Drawing Sheets

RECOVERY OF STYRENE FROM PYROLYSIS GASOLINE BY EXTRACTIVE DISTILLATION

This application is a continuation of application Ser. No. 08/651,707, filed on May 21, 1996, which was abandoned upon the filing hereof.

BACKGROUND OF THE INVENTION

In one aspect, this invention relates to the separation of selected compounds in a pyrolysis gasoline stream mainly comprising substituted unsaturated aromatics. The selected compounds are separated from close-boiling aromatic and non-aromatic hydrocarbons by extractive distillation. In another aspect, this invention relates to the use of a mixture of sulfolane (tetramethylene sulfone) alone or in combination with water as the solvent (also referred to as extractant or entrainer) in the aforementioned extractive distillation.

Extractive distillation is a well-known technique for separating mixtures of components having a relative volatility close to unity (i.e., having nearly equal volatility and having nearly the same boiling point). It is difficult to separate the components of such mixtures by conventional fractional distillation. In extractive distillation, a solvent is introduced into a distillation column above the entry point of the feed mixture which is to be separated. The presence of the solvent in the column alters the relative volatility of the compounds present in a direction to make the separation greater, and thus, to require either fewer stages to effect the same separation or to make possible a greater degree of separation with the same number of stages. The solvent affects the volatility of the higher boiling feed component(s) sufficiently to facilitate the separation of the various feed components, and it exits with the bottoms fraction, as has been described in the article entitled "*Extractive Distillation Saves Energy*" by Ian Sucksmith. Chemical Engineering, Jun. 28, 1982, pages 91–95. Other literature sources on extractive distillation techniques include the "*Handbook of Separation Techniques for Chemical Engineers*" by Philip A. Schweitzer, McGraw-Hill Book Company, 1979, pages 1-135 to 1-143; and *Perry's Chemical Engineers Handbook*, 6th Edition, McGraw-Hill Book Company, 1984, pages 13-53 to 13-57.

The separation of substituted unsaturated aromatics, in particular styrene, from a close-boiling aromatic and non-aromatic hydrocarbon mixture (pyrolysis gasoline) by extractive distillation is known and has been described in patent literature, such as in U.S. Pat. Nos. 3,684,665; 3,763,015; 2,480,919; 4,031,153; more/less 3,328,267; 2,467,197; 2,385,235; 2,380,019 and 3,210,259. The separation of styrene from specific compounds found in the pyrolysis gasoline stream, namely the separation of styrene from ethyl benzene or o-xylene by extractive distillation is also described in the patent literature, such as in U.S. Pat. No. 4,966,656. However, there is a need for the development of more selective solvents than those presently known in the extractive distillation of pyrolysis gasoline components. In particular, it is desirable to develop improved extractive distillation processes for producing styrene of high purity, both with more selective solvents and by other techniques, since this compound is an important starting material for various plastics.

SUMMARY OF THE INVENTION

It is an object of this invention to provide a process to produce high purity substituted unsaturated aromatic compounds, especially styrene, from a pyrolysis gasoline stream containing close-boiling aromatic and non-aromatic hydrocarbons by extractive distillation employing a selective solvent (also referred to as an extractant or entrainer). It is another object of this invention to provide a novel extractant mixture comprising a hydrocarbon solvent(s) and water.

Further in accordance with this invention, a process is provided for separating at least one selected substituted unsaturated aromatic, preferably styrene, from pyrolysis gasoline by extractive distillation from a pyrolysis gasoline feed containing a significant amount of such aromatic(s), which employs a preferred solvent consisting essentially of sulfolane, in a mixture with water.

Still further in accordance with the invention, processes are provided consisting of multiple steps to produce high quality styrene from a pyrolysis gasoline feed stock.

In accordance with a preferred embodiment of the invention, a process is provided for separating at least one substituted unsaturated aromatic hydrocarbon from at least one close-boiling aromatic or non-aromatic hydrocarbon by extractive distillation of a feed containing at least one substituted unsaturated aromatic and at least one close-boiling aromatic or non-aromatic hydrocarbon, by employing a solvent consisting essentially of two components. The process produces an overhead product containing a smaller volume percentage of the at least one substituted unsaturated aromatic and a larger volume percentage of the at least one aromatic or non-aromatic hydrocarbon than the feed; and a bottoms product containing a solvent and a larger volume percentage of the at least one substituted unsaturated aromatic and a smaller volume percentage of the at least one aromatic or non-aromatic hydrocarbon than the feed. The at least one substituted unsaturated aromatic is separated from the solvent and recovered from the bottoms product.

Preferably one component of the solvent is selected from the group consisting of propylene carbonate, sulfolane (tetramethylene sulfone), methyl carbitol, 1-methyl-2-pyrrolidinone,2-pyrrolidinone, and mixtures thereof, and the other component of the solvent is water. The preferred component of the solvent from the group of organic components listed is sulfolane.

In another preferred embodiment, the at least one substituted unsaturated aromatic in the feed is styrene and the at least one aromatic or non-aromatic hydrocarbon is o-xylene.

The preferred range for the weight ratio of solvent to feed is in the range of about 05:1 to about 50:1, more preferably 2:1 and 20:1. It is also preferred that the feed boil at a temperature in the range of about 100° C. to 180° C.

The boiling point of said at least one substituted unsaturated aromatic and the boiling point of said at least one aromatic or non-aromatic hydrocarbon may preferably differ by about 0.1° to 10° C.

In further accordance with the invention, a process is provided for separating styrene from at least one close-boiling aromatic or non-aromatic hydrocarbon by extractively distilling a mixture thereof in the presence of a two-part extractive solvent the first part of which is selected from the group consisting of propylene carbonate, sulfolane (tetramethylene sulfone), methyl carbitol, 1-methyl-2-pyrrolidinone, 2-pyrrolidinone, and mixtures thereof, and the second part of which is water, to obtain a solvent fraction relatively rich in styrene, and stripping styrene from said solvent fraction. It is particularly preferred that the at least one close-boiling aromatic or non-aromatic hydrocarbon is o-xylene. It is also preferred that the weight proportion of the second part of said extractive solvent to the first part thereof is from about 0% to about 20%.

In accordance with another aspect of the invention, a process is provided for producing styrene from a feedstock comprising styrene and at least one close-boiling aromatic or non-aromatic hydrocarbon by feeding said feedstock into a distillation zone, feeding two-part extractive solvent into said distillation zone, said solvent consisting essentially of a first part selected from the group consisting of propylene carbonate, sulfolane (tetramethylene sulfone), methyl carbitol, 1-methyl-2-pyrrolidinone, 2-pyrrolidinone, and mixtures thereof and a second part consisting of water, distilling said feedstock in said distillation zone in the presence of said extractive solvent to produce a solvent fraction relatively rich in styrene compared to the solvent fed to said distillation zone, and an overhead fraction comprising said at least one close-boiling aromatic or non-aromatic hydrocarbon and being relatively lean in styrene compared to said feedstock, withdrawing said solvent fraction from said distillation zone and withdrawing said overhead fraction from said distillation zone.

In a preferred form of said process, the two parts of said two-part extractive solvent are fed to said distillation zone separately. The preferred feedstock is pyrolysis gasoline.

A further preferred embodiment of the invention is one in which said feedstock is formed by fractionating a pyrolysis gasoline to produce a $C_8$ stream comprised mainly of hydrocarbons containing 8 carbons, said $C_8$ stream constituting the feedstock fed to said distillation zone. Furthermore, said $C_8$ stream may be hydrogenated before being fed to said distillation zone to hydrogenate any acetylenic compounds therein, and the hydrogenation of said $C_8$ stream is preferably effected under conditions avoiding conversion of substantial amounts of styrene to ethylbenzene.

It is further preferred that the invention be practiced in such a way that at least a portion of said overhead fraction is hydrogenated to produce a mixture containing toluene and xylene.

In addition, the above-mentioned solvent fraction is desirably fed to a stripping zone in which styrene, a portion of said aromatic or non-aromatic hydrocarbon, and water are separated into a stripper overhead stream from solvent, which then constitutes a lean solvent bottom stream, and which is recycled to said distillation zone as the first part of said two-part extractive solvent. Further, the stripper overhead stream is preferably fed to a styrene purification zone in which hydrocarbon components, including cyclopentadiene, which are lighter than styrene and water, are separated into a styrene purifier overhead stream, purified styrene is separated into a styrene purifier side stream, and a styrene purifier bottom stream containing some of the first part of said extractive distillation solvent is formed in said styrene purifier zone. The styrene purifier bottom stream is then preferably treated to recover a portion of the first part of said extractive distillation solvent for reuse in said process.

Furthermore, in the above-described processes, water is preferably separated from the overhead streams issuing from said extractive distillation zone, said stripping zone, and said styrene purification zone, and is returned to said distillation zone as at least a portion of said second part of said two-part extractive solvent.

Preferably, the weight ratio of said two-part extractive solvent to said feedstock is between about 1:1 and about 20:1, the feedstock boils at a temperature in the range of from about 100° C. to about 180° C., and the boiling point of said styrene and said at least one close-boiling aromatic or non-aromatic hydrocarbon differ by from about 0.1° C. to about 10° C.

Other objects and advantages will be apparent from the detailed description of the invention which follows, and the appended claims.

DETAILED DESCRIPTION OF THE INVENTION

In an extractive distillation process, an agent (called "solvent" or "extractant" or "entrainer") is added to a feed mixture of components to be separated, so that the relative volatilities of the components of the mixture are changed such that a sufficient difference in volatility of the components results, and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity causes great differences between the relative volatilities of the components in a mixture, and will allow for the separation of components in a mixture with fewer distillation stages, a lower amount of reflux, and higher product purity. The term "close-boiling" as used herein, means that the feed components have nearly the same boiling point at the conditions of the distillation.

Any hydrocarbon feed which contains at least one substituted unsaturated aromatic and at least one aromatic or non-aromatic hydrocarbon, which is close-boiling with it, can be used in the process of this invention.

Non-limiting examples of suitable feed components are styrene, o-xylene, cumene, toluene, dicyclopentadiene, p-xylene, ethylbenzene, 2,5-dimethylthiophene, 6,6-dimethylfulvene, phenylacetylene, m-xylene, isopropylbenzene, vinylnorbornenes and allylbenzene, all of which are common in pyrolysis gasolines. Such components may also be found in other hydrocarbon feedstocks such as coal tar liquids and catalytically reformed naphtha.

Any suitable weight ratio of the solvent to the hydrocarbon-containing feed mixture can be employed. Preferably, the solvent-to-feed weight ratio is in the range of about 0.5:1 to about 50:1, and more preferably between about 2:1 and about 20:1.

Any suitable total column height, packed column height, column diameter and number of trays in the extractive distillation column can be employed. The exact dimensions and column designs depend on the scale of the operation, the exact feed composition, the exact solvent composition, the desired recovery and the degree of purity of the sought-after substituted unsaturated aromatic product, and like considerations.

The following examples are presented to further illustrate the invention and are not to be considered as unduly limiting the scope of this invention.

EXAMPLE I

This example demonstrates the use of various solvents in the extractive distillation of a pyrolysis gasoline feed.

To a pyrolysis gasoline feed comprised of 5.3% toluene, 4.3% vinylnorbornene, 11.8% ethylbenzene, 3.3% p-xylene, 0.2% 2,5-dimethylthiophene, 5.5% o-xylene, 0.5% dicyclopentadiene, 27.9% styrene, 0.1% allylbenzene, and 0.3% 6,6-dimethylfulvene (in weight %), an extractive solvent was added at various solvent:feed ratios. The total mixture (including the extractive solvent) was heated under reflux conditions for about 20–60 minutes in a vapor-liquid equilibrium still containing one theoretical stage and equipped with a total reflux condenser. Prior to the addition of solvent, a feed and equilibrium vapor sample of the pyrolysis gasoline were taken. Solvent was added at 1:1 and 5:1 solvent: feed ratios to the still. After reaching equilibrium, a small condensed vapor sample was withdrawn by means of a septum located below the total reflux condenser. The sample was analyzed and the weight fractions of the feed components in the vapor phase were determined by gas chromatography. The relative volatility $R^1$ was calculated as follows:

$$R^1=(Y_1/Y_2)/(X_1/X_2)=(Y_1/X_1)/(Y_2/X_2)$$

wherein, in this example, $Y_1$ and $Y_2$ are the weight fractions of o-xylene and styrene respectively, in the vapor phase, and $X_1$ and $X_2$ are the weight fractions of o-xylene and styrene, respectively, in the liquid phase. O-xylene and styrene were chosen for this example because of the difficulty of their separation. Test results for these two compounds are summarized in Table I.

The following solvents were tested: 1-Methyl-2-pyrrolidinone, sulfolane, adiponitrile, 1-(2-aminoethyl) piperazine, n-formyl morpholine, 2-pyrrolidinone, propylene carbonate, methyl carbitol.

TABLE I

| Solvent:Feed Weight Ratio | Solvent | Relative Volatility ox/sty |
|---|---|---|
| 0:1 | No agent | 1.0 |
| 1:1 | 1-Methyl-2-Pyrrolidinone | 1.4 |
| 1:1 | Sulfolane | 1.4 |
| 1:1 | Adiponitriie | 1.3 |
| 1:1 | 1-(2-Aminoethyl) Piperazine | 1.2 |
| 1:1 | N-Formyl Morpholine | 1.3 |
| 1:1 | 2-Pyrrolidinone | 1.4 |
| 1:1 | Propylene Carbonate | 1.3 |
| 1:1 | Methyl Carbitol | 1.2 |
| 5:1 | 1-Methyl-2-Pyrrolidinone | 1.6 |
| 5:1 | Sulfolane | 1.7 |
| 5:1 | Adiponitrile | 1.4 |
| 5:1 | 1-(2-Aminoethyl) Piperazine | 1.3 |
| 5:1 | N-Formyl Morpholine | 1.5 |
| 5:1 | 2-Pyrrolidinone | 1.7 |
| 5:1 | Propylene Carbonate | 1.4 |
| 5:1 | Methyl Carbitol | 1.4 |

Test data in Table I clearly show that several of the extractive agents gave higher relative volatility data and thus are, in accordance with the invention, expected to be more effective as solvents (extractants) in the separation of substituted unsaturated aromatics, especially styrene, from close-boiling aromatic and non-aromatic hydrocarbons.

EXAMPLE II

This example demonstrates the extractive distillation of the feed mixture described in Example 1, with sulfolane employed as the extractive agent. The distillation setup was in accordance with that which was described in Example I. For this experiment, 75 grams of the pyrolysis gasoline feed was added to the vapor-liquid equilibrium still, and feed and vapor samples were taken and analyzed. Solvent was added at a 1:1 (75 grams added) and 5:1 (375 grams added) solvent: feed ratios to the still. After reaching equilibrium, a small condensed vapor sample was withdrawn by means of a septum located below the total reflux condenser. The sample was analyzed, and the weight fractions of the feed components in the vapor phase were determined by gas chromatography. Test results are summarized in Table II.

TABLE II

| Component | Description | Relative Volatility of A/B No Agent | Relative Volatility of A/B 1:1 Solvent[1]: feed | Relative Volatility of A/B 5:1 Solvent[1]: feed |
|---|---|---|---|---|
| A | o-Xylene | 1.0 | 1.4 | 1.7 |
|   | Toluene | 3.1 | 3.6 | 4.5 |
|   | Ethylbenzene | 1.4 | 1.8 | 2.2 |
|   | p-Xylene | 1.3 | 1.8 | 2.3 |
|   | 2,5-Dimethylthiophene | 1.3 | 1.7 | 2.1 |
|   | Dicyclopentadiene | 0.5 | 0.9 | 1.2 |
|   | 6,6-Dimethylfulvene | 0.6 | 0.6 | 0.6 |
|   | Vinylnorbornenes | 1.3 | 2.5 | 3.8 |
|   | Allylbenzene | 0.7 | 0.8 | 0.9 |
| B | Styrene |   |   |   |

[1]Employing Sulfolane as the extractive agent.

The results given in Example II can be compared to those results given in Example III, which involves the testing of 2-pyrrolidinone, a compound seen in Example I to give results equal to those produced by the use of sulfolane as the extractive agent where the desired separation was between o-xylene and styrene.

EXAMPLE III

This example demonstrates the extractive distillation of the feed mixture described in Example I, with 2-pyrrolidinone employed as the extractive agent. The distillation setup was in accordance with that which was described in Example I. For this experiment, 75 grams of the pyrolysis gasoline feed was added to the vapor-liquid equilibrium still, and feed and vapor samples were taken and analyzed. Solvent was added at 1:1 (75 grams added) and 5:1 (375 grams added) solvent: feed ratios to the still. After reaching equilibrium, a small condensed vapor sample was withdrawn by means of a septum located below the total reflux condenser. The sample was analyzed, and the weight fractions of the feed components in the vapor phase were determined by gas chromatography. Test results are summarized in Table III.

TABLE III

| Component | Description | Relative Volatility of A/B No Agent | Relative Volatility of A/B 1:1 Solvent[1]: feed | Relative Volatility of A/B 5:1 Solvent[1]: feed |
|---|---|---|---|---|
| A | o-Xylene | 1.0 | 1.4 | 1.7 |
|  | Toluene | 3.1 | 4.0 | 4.3 |
|  | Ethylbenzene | 1.4 | 1.8 | 2.2 |
|  | p-Xylene | 1.3 | 1.8 | 2.2 |
|  | 2,5-Dimethylthiophene | 1.3 | 1.7 | 2.0 |
|  | Dicyclopentadiene | 0.5 | 0.8 | 1.1 |
|  | 6,6-Dimethylfulvene | 0.6 | 0.6 | 0.7 |
|  | Vinylnorbornenes | 1.3 | 2.4 | 3.5 |
|  | Allylbenzene | 0.7 | 0.8 | 0.9 |
| B | Styrene |  |  |  |

[1]Employing 2-Pyrrolidinone as the extractive agent.

Based on the test results shown in Table II and Table III, it appears that both sulfolane and 2-pyrrolidinone had similar selectivity. However, sulfolane is selected as the preferred solvent because of its higher boiling point for the separation of substituted unsaturated aromatics, in particular styrene, from close-boiling aromatic and non-aromatic hydrocarbons.

EXAMPLE IV

This example illustrates the use of a mixture of water and sulfolane as solvent in the extractive distillation of styrene from the pyrolysis gasoline feed.

This example demonstrates the extractive distillation of the feed mixture described in Example I, with a mixture of sulfolane and water employed as the extractive agent. The distillation setup was in accordance with that which was described in Example I. For this experiment, 25 grams of the pyrolysis gasoline feed was added to the vapor-liquid equilibrium still, and feed and vapor samples were taken and analyzed. Solvent was added at 5:1 (125 grams added) and 10:1 (250 grams added) solvent:feed ratios to the still. Water was also added to the still, and was maintained at 3 weight % of the total solvent mass at all feed ratios. After reaching equilibrium, a small condensed vapor sample was withdrawn by means of a septum located below the total reflux condenser. The sample was analyzed, and the weight fractions of the feed components in the vapor phase were determined by gas chromatography. Test results are summarized in Table IV.

TABLE IV

| Component | Description | Relative Volatility of A/B No Agent | Relative Volatility of A/B 5:1 Solvent[1]: feed | Relative Volatility of A/B 10:1 Solvent[1]: feed |
|---|---|---|---|---|
| A | o-Xylene | 1.0 | 1.8 | 1.8 |
|  | Toluene | 2.9 | 4.6 | 4.2 |
|  | Ethylbenzene | 1.4 | 2.4 | 2.5 |
|  | p-Xylene | 1.3 | 2.4 | 2.5 |
|  | 2,5-Dimethylthiophene | 1.3 | 2.1 | 2.2 |
|  | Dicyclopentadiene | 0.5 | 1.4 | 1.6 |
|  | 6,6-Dimethylfulvene | 0.6 | 0.6 | 0.6 |
|  | Vinylnorbornenes | 1.3 | 4.4 | 4.9 |
|  | Allylbenzene | 0.7 | 0.9 | 1.0 |
| B | Styrene |  |  |  |

[1]Employing Sulfolane + 3% water as the extractive agent.

Based on the test results shown in Table II and Table IV, it is concluded that sulfolane (tetramethylene sulfone) is more effective when in a mixture with water as the solvent for the separation of substituted unsaturated aromatics, in particular styrene, from close-boiling aromatic and non-aromatic hydrocarbons.

EXAMPLE V

Using the selected extractive solvent mixture of sulfolane and water, pilot plant tests were conducted in a 3-inch diameter stainless steel extractive distillation column packed with 24 feet of knitted wire mesh stainless steel packing (Goodloe® Style #773). The column was well-insulated to prevent heat loss. A double loop thermosiphon reboiler with a maximum heat input capacity of 4000 watts was used to generate liquid boil-up in the column. A condenser was used to condense the overhead vapor. A part of condensed liquid from the receiver was refluxed back to the top of extractive distillation column and the remainder of the liquid was taken from the receiver as the raffinate product. The detailed configuration of the extractive distillation column is shown in FIG. 1.

Figure 1:
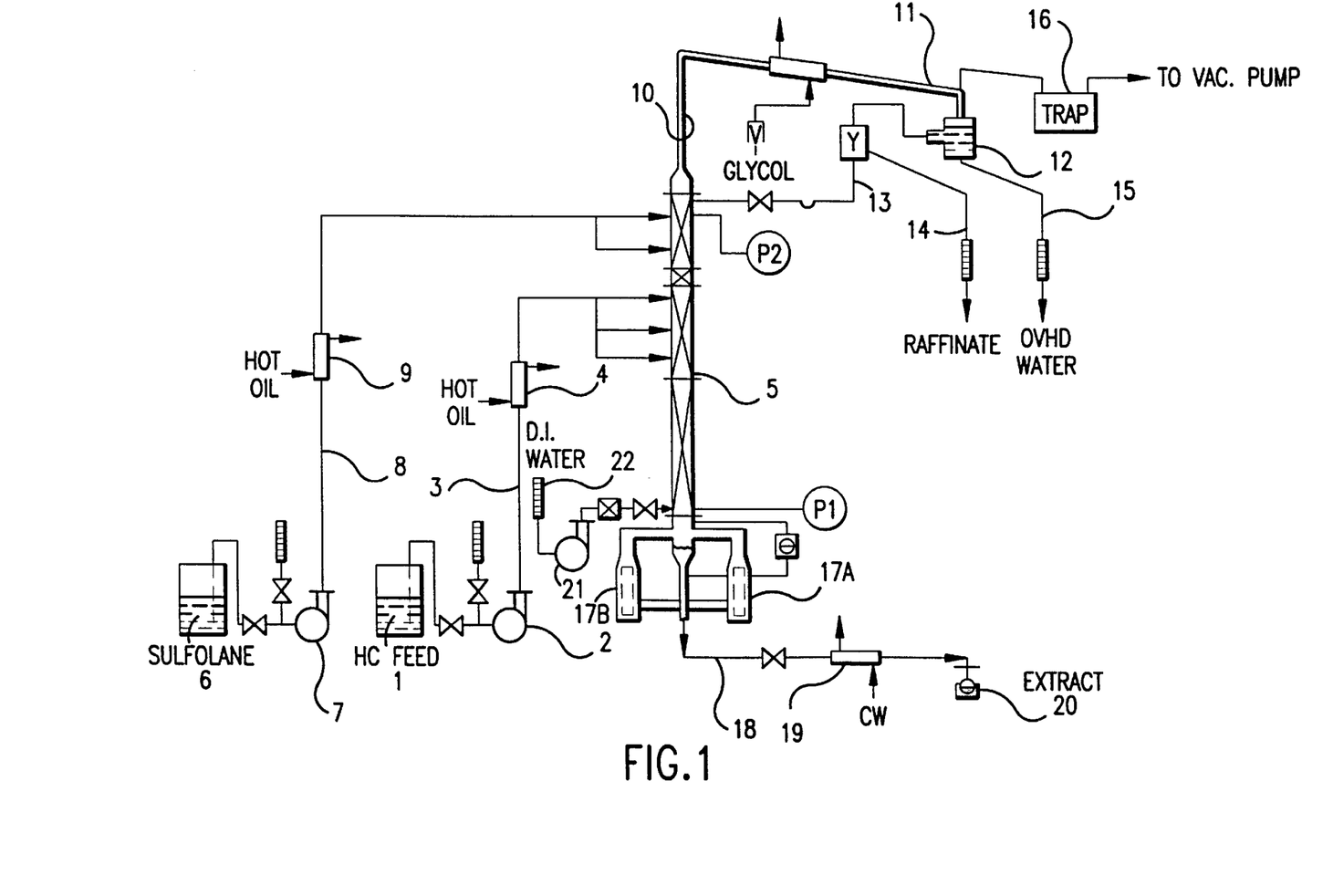
FIG. 1 is a diagrammatic elevational view of part of a pilot plant in which portions of the process of the invention were practiced.

In FIG. 1, the pyrolysis gasoline feed (hydrocarbon feed) was transferred by pump 2 from feed storage tank 1 through 3 lines to extractive distillation column 5 at a rate of 45 ml/min. The stream was heated by hot oil (or steam may be used) in heat exchanger 4° to 58° C. before entering extractive distillation column 5 at a location fourteen (14) feet from the column bottom. The feed composition is given in Table V. Sulfolane containing 0.1 to 0.3 wt % water was fed by pump 7 through line 8 to extractive distillation column 5 at a location twenty one (21) feet from the bottom of the column. Sulfolane was fed at a rate of 435 m/min. and the stream was heated to 59° C. by hot oil in heat exchanger 9. Deionized water was introduced to extractive distillation column 5 at just above the reboiler, by pump 21 through line 22 at a rate of 20 ml/min. The column was operated under reduced pressure (65 mmHg absolute) and the vacuum was generated by a vacuum pump.

Approximately 3200 to 3500 watts was used at the reboiler to generate the liquid boil-up in the column. The raffinate vapor stream exited at the top of extractive distillation column 5 through vapor line 10 and was condensed by cooler 11, using a glycol/water mixture as the coolant. The condensed raffinate liquid was transferred through line 11a to the overhead receiver 12, where hydrocarbon and water were separated. A portion of the hydrocarbon phase was refluxed back to the column at a reflux ratio of 0.3:1.0 via line 15 and the remainder was taken via line 14 as the raffinate product (at 37 ml/min.). The water phase was removed from the receiver 12 by level control. At steady state operation, the pressure drop in extractive distillation 10 column 5 was around 16 to 18 mmHg. The extract stream from the bottom of extractive distillation column 5 contained 99.3 wt % sulfolane, 0.68 wt % styrene, 1 ppmw or less o-xylene, 15 ppmw or less allylbenzene, and less than 0.1 wt % water. The composition of the extract and raffinate streams are presented in Table V.

Figure 2:
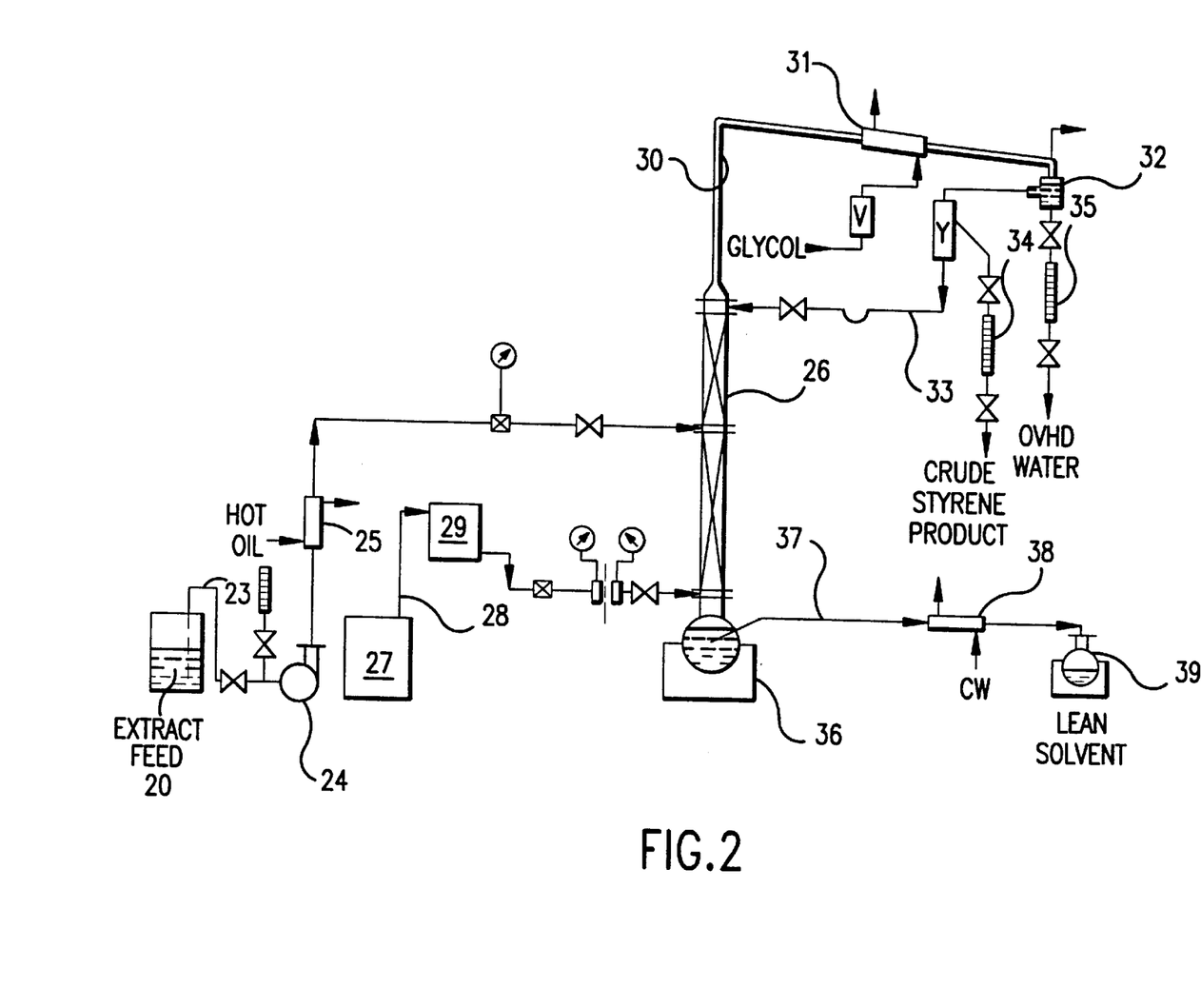
FIG. 2 is a simplified diagrammatic elevational view of the stripper portion and associated equipment of the pilot plant of FIG. 1.

Sulfolane solvent was recovered by stream stripper 26 shown in FIG. 2. This system contained: a 3-inch diameter column packed with 6 feet of Gempak® 4BG corrugated structured stainless steel packings in the stripping section and 4 feet of Goodloe® knitted wire mesh stainless steel packings (Style #779) in the rectification section; an offset condenser and decanter; an overhead water collection system; a reflux splitter on the crude styrene product stream; a feed preheating and metering system; and a stripped solvent collection system.

As shown in FIG. 2, extract stream from extractive distillation column 5 (rich solvent) (FIG. 1) was fed from extract tank 20 by pump 24 through line 23 to stream stripper 26. The extract stream was fed at a rate of 700 ml/min. and heated to 93° to 95° C. by heat exchanger 25 before entering stream stripper 26. Approximately 75 grams/min. of water was transferred from water tank 27 through line 28 to steam generator 29 to generate superheated steam at 200° C., which was fed to the bottom of steam stripper 26. The kettle had a capacity of 12 liters and was maintained at 160° C. by a heating mantle. The stripper was operated at 70 mmHg absolute pressure.

The overhead vapor stream was removed through line 30 and condensed by cooler 31 before discharging to the overhead receiver 32, where a portion of the hydrocarbon phase was refluxed back via line 33 to the stripper at a reflux ratio of 2:1. The rest of the condensate was taken off as the crude styrene product through line 35, at a rate of 12 to 14 ml/min. The overhead steam condensate was withdrawn from receiver 32 through line 35 at a rate of 56 to 65 ml/min. The lean solvent containing 99.8 wt % sulfolane, 0.1 to 0.3 wt % water, and trace amount of hydrocarbons, was withdrawn from the kettle through line 37, cooled by cooler 38, and then discharged to vessel 39 at a rate of 680 to 690 ml/min. The crude styrene product from line 34 contained 99.9 wt % styrene.

Figure 3:
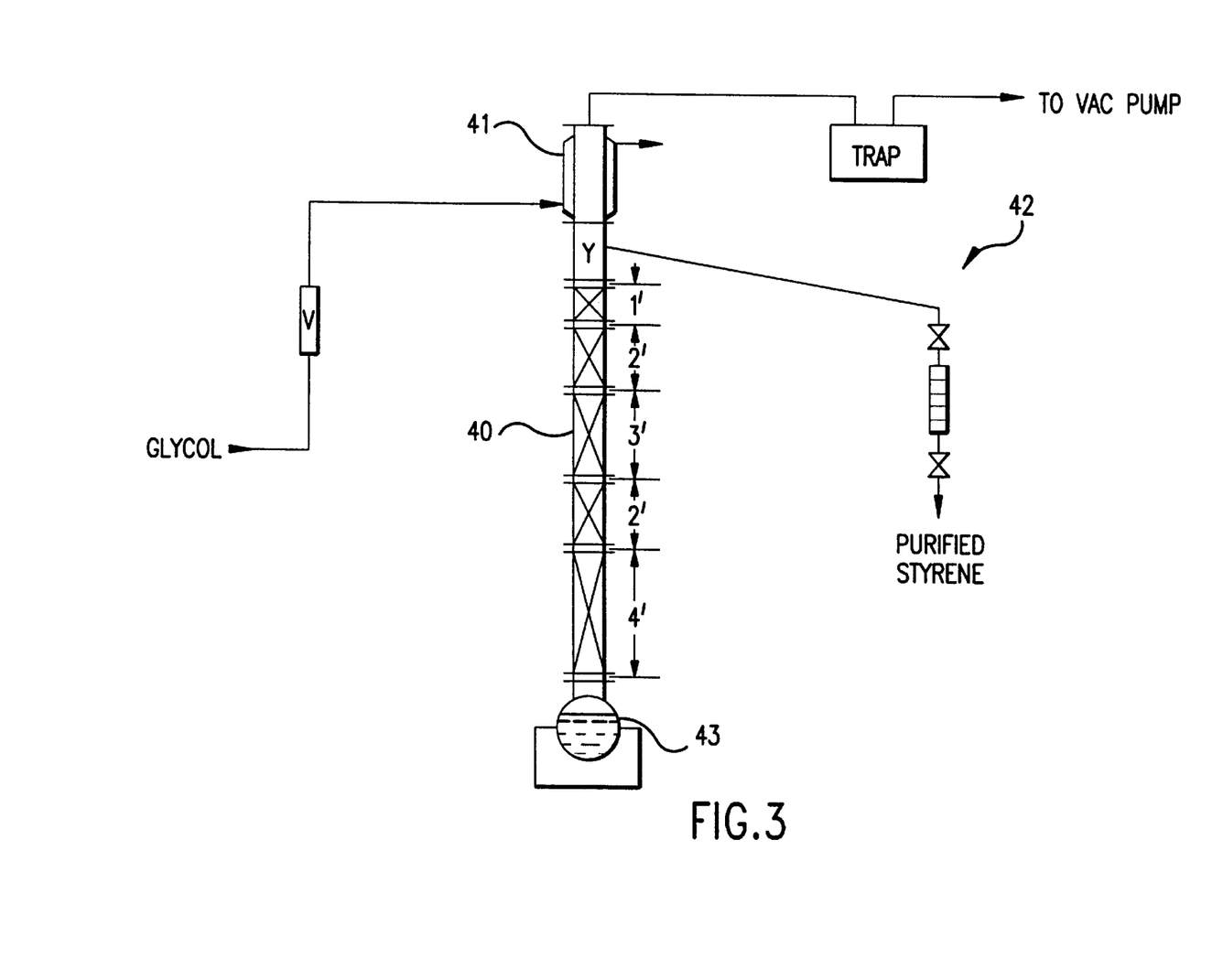
FIG. 3 is a simplified diagrammatic elevational view of a further portion of the pilot plant comprising a batch distillation column for further purifying the styrene obtained in the process of the invention as practiced in FIGS. 1 and 2.

In order to remove the trace amounts of heavy components from the crude styrene, and to improve the product color, batch distillation was carried out to distill the purified styrene to the overhead of the column. A sketch of the batch distillation column 40 is shown in FIG. 3. A 3-inch diameter column 40 was employed. It had 12 feet of Goodloe® knitted wire mesh stainless steel packings (Style #773) in it. The system also included an in-line reflux splitter and condenser 41, an overhead product collection system 42, and a 12 liter kettle 43 with an electric heating mantle for reboiler heat input. At a 5:1 reflux ratio, 75° C. kettle temperature, and 49 mmHg absolute column pressure, the purified styrene with 99.9+% purity was recovered from the overhead of the column.

TABLE V

| DESCRIPTION | FEED | OVERHEAD | BOTTOMS |
| --- | --- | --- | --- |
| Dicyclopentadiene | 0.26 | 0.40 | <1 PPM |
| Benzene | 0.22 | 0.23 | <1 PPM |
| Toluene | 35.81 | 36.54 | <1 PPM |
| Vinylnorbornenes | 3.73 | 3.95 | <1 PPM |
| Ethylbenzene | 12.03 | 13.47 | <1 PPM |
| p-Xylene | 2.97 | 3.13 | <1 PPM |
| m-Xylene | 7.45 | 7.84 | <1 PPM |
| Cumene | 395 PPM | 431 PPM | <1 PPM |
| o-Xylene | 4.52 | 5.79 | <1 PPM |
| Styrene | 23.82 | 18.91 | 0.68 |
| Allylbenzene | 390 PPM | 573 PPM | 15 PPM |
| Water | 0.076 | <50 PPM | 0.0109 |
| Non-aromatics | 8.93 | 9.57 | <1 PPM |
| 2,5 Dimethylthiophene | 172 PPM | 195 PPM | <1 PPM |
| Solvent (Sulfolane) | 0 | 0.37 | 99.3 |

Figure 4:
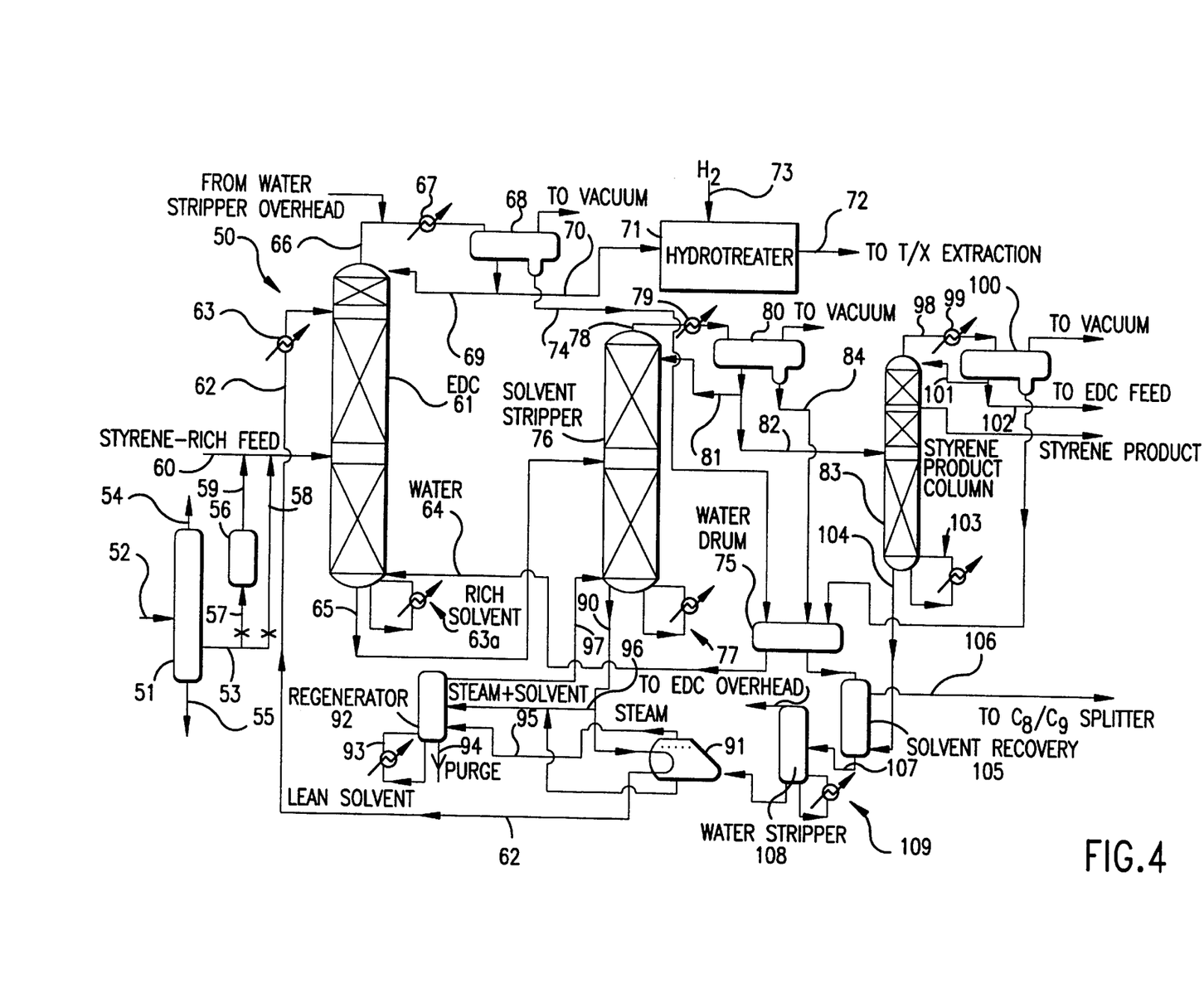
FIG. 4 is a simplified diagrammatic elevational view of an industrial plant for practicing the processes of the invention.

FIG. 4 is a diagrammatic illustration in elevation of an industrial plant for practicing the present invention. A preferred, but optional, element of the plant 50 is a fractionator 51, which is fed pyrolysis gasoline through line 52, and which effects a tight separation of $C_8$'s, which leaves the tower through line 53, with C-7 and lighter materials leaving the fractionator 51 through line 54, and C-9 and heavier materials leaving the tower as bottoms through line 55.

Preferably, but also optionally, the closely fractionated $C_8$ stream is fed through a hydrogenator 56 through line 57. The hydrogenation process carried out therein is mild enough to selectively hydrogenate any acetylenic compounds, such as phenylacetylene, without converting an objectionable proportion of the styrene to ethylbenzene. Since this step is optional, a bypass line 58 and appropriate valving are shown for omitting it. The output of the hydrogenator is fed through line 59, together with styrene-rich feed obtained through line 58, or from any other source through line 60, into the extractive distillation column 61. Column 61 is shown as a packed tower. Lean solvent is introduced to the tower through line 62 from portions of the plant to be discussed below. It is fed at a point above the feed of the styrene-rich material through line 60. Heat is applied to the tower by heater 63 in the lean solvent input line, and by reboiler circuit 63a at the bottom of the column. In accordance with the invention, water as a second component of the extractive distillation solvent is introduced into the extractive distillation column 61 through line 64.

In the extractive distillation column 61, the distillation conditions are so modified by the lean solvent and the water component that the styrene tends to flow downwardly through the tower to exit with the rich solvent through bottom line 65, while the other aromatics and the non-aromatics are distilled overhead through line 66. The aromatics in this stream are primarily $C_8$'s, i.e., ethylbenzene and meta-, ortho- and para-xylene, and the non-aromatic overhead material is primarily C-9 napthenes and C-9 paraffins. The overhead stream in line 66 is passed through condenser 67 to separator drum 68 where a portion of it is withdrawn and fed back as reflux through line 69. The balance of the organic part of the overhead condensate is fed through line 70 through hydrotreater 71, where it is hydrogenated to produce mixture which is primarily toluene/xylene that is fed through line 72 to a toluene/xylene extraction unit (not shown). Hydrogen for the hydrotreater is supplied through line 73. Water is drawn from the condensate drum 68 from a deep leg thereof through line 74, which feeds it to water drum 75.

The styrene-rich solvent from the bottom line 65 of the extractive distillation column 61 is fed to solvent stripper 76, which is also shown as a packed tower. Heat for stripping is supplied to the tower in part by reboiler circuit 77. In the solvent stripper 76, the separation of styrene from the solvent is effected, and the styrene leaves the stripper through overhead line 78. It is passed through condenser 79 into condensate drum 80. A portion of the condensate is withdrawn and fed through line 81 as reflux to the top of the stripper tower 76. The balance of the hydrocarbon stream is fed through line 82 to the styrene purification column 83. Water is withdrawn from a deep leg of the condensate drum 80 through line 84, which delivers it to water drum 75.

The bottom stream from solvent stripper 76 is lean solvent, which leaves the tower through line 90 and is passed through a steam generator 91 for removal of heat before being fed back to the extractive distillation column 61 through line 62. A solvent regenerator 92 is provided with a reboiler circuit 93 and a purge line 94. It receives some lean solvent through side draw line 96 from lean solvent line 90 and steam from generator 91 through line 95. The output of the regenerator 92 is fed back into the bottoms of the solvent stripper through line 97.

In the styrene purification column 83, which is also drawn as a packed tower, the components of the stripped and highly purified styrene stream are fed to the tower through line 82; those which are lighter than styrene are taken overhead through line 98 and passed through condenser 99, and are delivered to condensate drum 100. One material so removed is cyclopentadiene (CPD), the monomer of dicyclopentadiene (DCPD). This monomer tends to dimerize to DCPD, which in turn tends to crack back to CPD. Both CPD and DCPD are deleterious if left in the styrene product stream. The lighter overhead stream is drawn from condensate drum 100; a portion of it is fed back as reflux through line 101 and the remainder is fed through line 102 to be fed back into the extractive distillation column 61. A reboiler circuit 103 is provided at the bottom of column 83 to supply heat for operating the column. The bottom stream from purification column 83 is withdrawn through line 104 and includes residual traces of high boiling aromatic hydrocarbons, traces of polystyrene, and small amounts of other hydrocarbons, and traces of solvent. These are processed in a solvent recovery column 105; the top stream out of the solvent recovery column is delivered to a $C_8/C_9$ splitter through line 106, and the bottom stream is fed through line 107 to a water stripper 108. Water from water drum 75 is fed in part back to the base of the extractive distillation column 61, and in part to the top of the solvent recovery column 105. A water stripper column 108 is provided with a reboiler circuit 109. The overhead from the water stripper is fed back to join the overhead stream in line 66 out of the top of the extractive distillation column, while the bottom stream out of the water stripper is fed into boiler 91.

Purified styrene is separated into a styrene purifier side stream and withdrawn through the line marked "styrene product."

All of the fractionating columns are preferably operated under vacuum in order to lower the boiling points of the materials involved.

Reasonable variations, modifications and adaptations for various usages and conditions can be made within the scope of the disclosure and the appended claims, without departing from the scope of this invention.

That which is claimed is:

1. A process for producing styrene from a feedstock comprising styrene and at least one close-boiling aromatic or non-aromatic hydrocarbon comprising:
   feeding said feedstock into a single distillation column;
   feeding two-part extractive solvent into said distillation column, said solvent consisting essentially of a first part selected from the group consisting of propylene carbonate, sulfolane (tetramethylene sulfone), methyl carbitol, 1-methyl-2-pyrrolidinone, 2-pyrrolidinone, and mixtures thereof, but not including water, and a second part consisting of water, said two parts of said two-part extractive solvent being fed to said distillation column separately and independently at different locations along said single distillation column;
   distilling said feedstock in said distillation column in the presence of said extractive solvent to produce:
   (a) a solvent fraction relatively rich in styrene compared to the solvent fed to said distillation column; and
   (b) an overhead fraction comprising said at least one close-boiling aromatic or non-aromatic hydrocarbon and being relatively lean in styrene compared to said feedstock;
   withdrawing said solvent fraction from said distillation column; and
   withdrawing said overhead fraction from said distillation column.

2. A process in accordance with claim 1 in which said feedstock is pyrolysis gasoline.

3. A process in accordance with claim 1 in which said feedstock is formed by fractionating a pyrolysis gasoline to produce a $C_8$ stream comprised mainly of hydrocarbons containing 8 carbons, said $C_8$ stream constituting the feedstock fed to said distillation column.

4. A process in accordance with claim 3 in which said $C_8$ stream is hydrogenated before being fed to said distillation column to hydrogenate any acetylenic compounds therein.

5. A process in accordance with claim 4 in which said hydrogenation of said $C_8$ stream is effected under conditions avoiding conversion of substantial amounts of styrene to ethylbenzene.

6. A process in accordance with claim 1 in which said solvent fraction is fed to a stripping zone in which styrene, a portion of said aromatic or non-aromatic hydrocarbon and water are separated into a stripper overhead stream from solvent which constitutes a lean solvent bottom stream, and which is recycled to said distillation column as the first part of said two-part extractive solvent.

7. A process in accordance with claim 1 in which the weight ratio of said two-part extractive solvent to said feedstock is between about 1:1 and about 20:1.

8. A process in accordance with claim 1 in which said feedstock boils at a temperature in the range of from about 100° C. to about 180° C.

9. A process in accordance with claim 7 in which the boiling point of said styrene and said at least one close-boiling aromatic or non-aromatic hydrocarbon differ by from about 0.1° C. to about 10° C.

10. The process of claim 1, wherein said second part of the two-part extractive solvent is fed to said distillation column at a bottom portion of said distillation column.

11. A process for producing styrene from a feedstock comprising styrene and at least one close-boiling aromatic or non-aromatic hydrocarbon comprising:
   feeding said feedstock into a single distillation column;
   feeding two-part extractive solvent into said distillation column, said solvent consisting essentially of a first part selected from the group consisting of propylene carbonate, sulfolane (tetramethylene sulfone), methyl carbitol, 1-methyl-2-pyrrolidinone, 2-pyrrolidinone, and mixtures thereof, but not including water, and a second part consisting of water, said two parts of said two-part extractive solvent being fed to said distillation column separately and independently at different locations along said single distillation column;
   distilling said feedstock in said distillation column in the presence of said extractive solvent to produce:
   (a) a solvent fraction relatively rich in styrene compared to the solvent fed to said distillation column; and
   (b) an overhead fraction comprising said at least one close-boiling aromatic or non-aromatic hydrocarbon and being relatively lean in styrene compared to said feedstock;
   withdrawing said solvent fraction from said distillation column;
   withdrawing said overhead fraction from said distillation column; and
   in which at least a portion of said overhead fraction is hydrogenated to produce a mixture containing toluene and xylene.

12. The process of claim 11, wherein said second part of the two-part extractive solvent is fed to said distillation column at a bottom portion of said distillation column.

13. A process for producing styrene from a feedstock comprising styrene and at least one close-boiling aromatic or non-aromatic hydrocarbon comprising:

feeding said feedstock into a single distillation column;

feeding two-part extractive solvent into said distillation column, said solvent consisting essentially of a first part selected from the group consisting of propylene carbonate, sulfolane (tetramethylene sulfone), methyl carbitol, 1-methyl-2-pyrrolidinone, 2-pyrrolidinone, and mixtures thereof, but not including water, and a second part consisting of water, said two parts of said two-part extractive solvent being fed to said distillation column separately and independently at different locations along said single distillation column;

distilling said feedstock in said distillation column in the presence of said extractive solvent to produce:
  (a) a solvent fraction relatively rich in styrene compared to the solvent fed to said distillation column; and
  (b) an overhead fraction comprising said at least one close-boiling aromatic or non-aromatic hydrocarbon and being relatively lean in styrene compared to said feedstock;

withdrawing said solvent fraction from said distillation column;

withdrawing said overhead fraction from said distillation column; and in which said solvent fraction is fed to a stripping zone in which styrene, a portion of said aromatic or non-aromatic hydrocarbon and water are separated into a stripper overhead stream from solvent which constitutes a lean solvent bottom stream, and which is recycled to said distillation column as the first part of said two-part extractive solvent; and in which said stripper overhead stream is fed to a styrene purification zone in which hydrocarbon components, including cyclopentadiene, and water are separated into a styrene purifier overhead stream, purified styrene is separated into a styrene purifier side stream, and a styrene purifier bottom stream containing some of the first part of said extractive distillation solvent is formed in said styrene purifier zone.

14. A process in accordance with claim 13 in which said styrene purifier bottom stream is treated to recover a portion of the first part of said extractive distillation solvent for reuse in said process.

15. A process in accordance with claim 13 in which water is separated from the overhead streams from said extractive distillation column, said stripping zone, and said styrene purification zone, and returned to said distillation column as at least a portion of said second part of said two-part extractive solvent.

16. The process of claim 13, wherein said second part of the two-part extractive solvent is fed to said distillation column at a bottom portion of said distillation column.

* * * * *

UNITED STATES PATENT AND TRADEMARK OFFICE
CERTIFICATE OF CORRECTION

PATENT NO. : 5,849,982
DATED : December 15, 1998
INVENTOR(S) : Fu-Ming Lee et al.

It is certified that error appears in the above-indentified patent and that said Letters Patent is hereby corrected as shown below:

| | | |
|---|---|---|
| Column 5, line 15 | Delete "5.3%" | Insert --35.3%-- |
| Column 8, line 24 | Delete "3 lines" | Insert --line 3-- |
| Column 8, line 51 | Delete "10" | |

Signed and Sealed this

Fourth Day of May, 1999

Attest:

Q. TODD DICKINSON

Attesting Officer

Acting Commissioner of Patents and Trademarks